United States Patent [19]

Nakamura et al.

[11] Patent Number: 4,636,471
[45] Date of Patent: Jan. 13, 1987

[54] **BIOCHEMICAL METHOD FOR PREPARATION OF OPTICALLY ACTIVE CARNITINE *ENTEROBACTER* SP. Y-239-B**

[75] Inventors: Usao Nakamura, Sakai; Makoto Takao, Kobe; Etsuko Ueno, Itami; Kichitaro Kawaguchi, Nara, all of Japan

[73] Assignee: Hamari Chemicals Ltd., Osaka, Japan

[21] Appl. No.: 597,233

[22] Filed: Apr. 5, 1984

[30] Foreign Application Priority Data

Apr. 5, 1983 [JP] Japan ................................... 58-60412

[51] Int. Cl.⁴ .............................................. C07P 41/00
[52] U.S. Cl. ..................................... 435/280; 435/128
[58] Field of Search ...................... 435/120, 128, 280; 562/567

[56] References Cited

U.S. PATENT DOCUMENTS 4,371,618 2/1983 Cavazza ............................. 435/128

OTHER PUBLICATIONS

Fujita et al., (1961), Chemical and Pharmaceutical Bulletin, vol. 9, No. 9, pp. 661–665.
Dunn et al., (1981), The Journal of Biological Chemistry, vol. 256, No. 23, pp. 12437–12444.
Vandecosteele, (1980), Applied and Environmental Microbiology, vol. 39, No. 2, pp. 327–334.

*Primary Examiner*—Sam Rosen
*Assistant Examiner*—William J. Herald
*Attorney, Agent, or Firm*—Burgess, Ryan & Wayne

[57] ABSTRACT

L-carnitine is produced by bringing apocarnitine into contact with hydrase produced by a strain of Enterobacter in an aqueous medium having a pH of 4–10 at a temperature of 20°–60° C., whereby apocarnitine is converted to L-carnitine.

7 Claims, No Drawings

BIOCHEMICAL METHOD FOR PREPARATION OF OPTICALLY ACTIVE CARNITINE *ENTEROBACTER* SP. Y-239-B

The present invention relates to the production of optically active carnitine by the action of an enzyme produced by a microorganism on apocarnitine.

L-carnitine is a substance which exhibits various pharmacological activities, particularly the activity of hyperfunction for digestion, and is in use as a medicine. L-carnitine that is currently used as a medicine is produced by the optical resolution of a racemate obtained through chemical reaction processes. However, the said resolution process requires costly optical resolving agents and involves complex procedures and thus it is desired to develop a cheaper production process.

Under these circumstances, the present inventors conducted investigation into the production of optically active carnitine by means of biochemical procedure.

As the reaction that biochemically yields L-carnitine, there have been conventionally known the hydroxylation of 4-N-trimethylaminobutyric acid (J. Biol. Chem., vol. 256, pp. 12437 to 12444, 1981), the reduction of 3-dehydrocarnitine (Appl. Environ. Microbiol., vol. 39, pp. 329 to 334, 1980) and so forth. Nevertheless, these processes suffer from the disadvantages that the required raw materials are costly and the used enzyme are unstable, and cannot be put into practical use.

The present inventors, after investigation into the cheaper production process for optically active carnitine, found the process which uses an enzyme produced by a microorganism to convert apocarnitine into L-carnitine through the reaction so far unknown, and have come to establish the present invention.

An aspect of the invention is directed to a process for preparing L-carnitine which comprises bringing apocarnitine into contact with water in the presence of hydrase capable of hydrating apocarnitine in an aqueous medium having a pH of 4–10 at a temperature of 20°–60° C. for an effective period of time to convert apocarnitine to L-carnitine and recovering L-carnitine from the aqueous medium.

Another aspect of the invention is directed to a composition for producing L-carnitine which comprises an aqueous medium containing apocarnitine and hydrase in an amount effective to convert aprocarnitine to L-carnitine, and hydrase having been produced by a strain of Enterobacter.

A further aspect of the invention is directed to a composition for recovering L-carnitine which comprises an aqueous medium containing L-carnitine converted from apocarnitine and hydrase produced by a strain of Enterobacter, the hydrase being able to convert apocarnitine to L-carnitine.

In the following, the present invention is described in more detail:

As the hydrase in the present invention, a hydrase produced by a microorganism is generally employed. And as the microorganism, use may be made of any of microorganisms which can produce the hydrase being able to convert apocarnitine to L-carnitine.

For example, there may be mentioned a microorganism, the strain No. Y-239-b, which the present inventors separated from the nature.

The strain shows the following properties:
(1) Morphological properties
  Shape: Short rod
  Size: 0.8–1.2×1.2–1.6
  Occrrence: Sigle
  Flagellum: Present
  Motility: Present
  Spore: None
  Gram-stain: Negative
  Acid-fast stain: Negative
(2) State of growth
  (a) Incubation on a meat extract-agar plate
    Form: Circular
    Elevation: Convex
    Margin: Entire
    Surface: Smooth
  (b) Incubation on a meat extract-agar slant
    Type of growth: Moderate
    Surface: Smooth
    Form of growth: Thready
    Color: Paraffin-like
    Gloss: Present
    Transparency: Translucent
  (c) Incubation on a meat extract liquid A
    Surface growth: None
    Turbidity: Moderate
    Precipitates: Moderate
(3) Physiological properties
  Liquidation of gelatin: Negative
  Litmus-milk coagulation: Negative
  pH of litmus milk: Acid
  Nitrate reduction: +
  Denitration reaction: −
  MR test: +
  VP test: +
  Production of indole: −
  Production of hydrogen sulfite: +
  Hydrolysis of starch: −
  Utilization of citric acid: + (Koser's medium)
  Utilization of citric acid: + (Christensen's medium)
Utilization of inorganic nitrogen sauces (growth)
  Ammonium sulfate: +
  Ammonium chloride: +
  Ammonium nitrate: +
  Potassium nitrate: +
  L-Asparagine: +
  L-glutamic acid: +
  Chromogenisis: −
  Urease: +
  Oxidase: −
  Catalase: +
  pH of growth: 4 to 10
  Optimum temperature of growth: 35° to 37° C.
  Oxygen tolerance: Anaerobic
  O-F test: Fermentation

| Production of acid and gas from saccharides | | |
|---|---|---|
| Saccharides | Acid | Gas |
| L-Arabinose | + | + |
| D-Xylose | + | + |
| D-Glucose | + | + |
| D-Mannose | + | + |
| D-Fructose | + | + |
| D-Galactose | + | + |
| Maltose | + | + |
| Sucrose | + | + |
| Lactose | + | + |
| Trehalose | + | + |
| D-Sorbitol | + | + |
| D-Mannitol | + | + |
| Inositol | + | − |
| Glycerine | + | + |

| Production of acid and gas from saccharides | | |
| --- | --- | --- |
| Saccharides | Acid | Gas |
| Starch | − | − |
| L-Sorbose | + | + |
| L-Rhamnose | + | + |
| D-Cellobiose | + | + |
| Raffinose | + | + |
| Sextrine | − | − |
| Dextran | − | − |
| Oxydation of gluconic acid | + | |
| Decomposition of malonic acid | − | |
| Decomposition of arginine | − | |
| Decarboxylation of lysine | − | |
| Decarboxylation of ornitine | − | |
| Decarboxylation of glutamic acid | − | |
| Deamination of phenylalanine | − | |
| Tolerance to sodium chloride | 2 to 50% | |
| Tolerance to potassium cyanide | + | |
| Auxotrophy | Biotin, pantotheinic acid | |

Identification in accordance with the classification described in Bergey's Manual of Determinative Bacteriology (7th edition) indicates that the microorganism showing the above bacteriological properties belongs to the genus enterobacter, and it has been decided that the microorganism is refered to as Enterobacter sp. Y-239-b. The said strain has been deposited at Fermentation Research Institute, Agency of Industrial Science & Technology with the deposit number FERM BP-510. The strain Y-239-b is susceptible to change in properties, and undergo mutations to be brought about by artificial mutagenic means using ultraviolet rays, X-rays, microwave, chemicals, etc., and even the mutants of the strain thus obtained, when they produce the hydrase capable of catalizing the conversion of apocarnitine into L-carnitine, can be employed in the process of the present invention.

The said strain or mutants may be cultivated on a culture medium containing nutrients which can normally be utilized by microorganisms. As the nutrient sources, known materials used for cultivating bacteria can be employed.

The culture medium may contain the carbon source such as glucose sucrose, starch, dextrin, molasses, organic acids, etc. and the nitrogen source such as urea, ammonium chloride, peptone, meat extract, yeast extract, etc. as well as inorganic salts such as salts of phosphoric acid, magnesium, potassium, sodium, calcium, manganese, zinc, copper, iron, molybdic acid and so forth.

With reference to the cultural method, the cultivation may be conducted under aerobic conditions at 25° to 30° C. for 24 to 72 hours, whereby the enzyme, hydrase, being able to catalyze the conversion of apocarnitine into carnitine is produced. The said hydrase is accumulated in the filtrate of the culture broth as well as in the microbial cells (solid component). In the present invention, apocarnitine is brought into contact with water in the presence of the hydrase.

The catalytic reaction of the hydrase can suitably be carried out normally at a pH of 4 to 10 and at a temperature of 20° to 60° C., and the reaction time varies depending upon the titer, concentration, etc. of the enzyme.

In conducting the reaction, the enzyme may be employed in the form of the culture broth including microbial cells; the culture broth having the microbial cells separated; the separated cells; crushed cell solutions obtained by grinding, autolyzing or disintegrating with ultrasonic waves the separated cells; cell-free extracts obtained by subjecting such crushed cell solutions to treatment such as centrifugation, salting out and precipitation; solid materials produced from such cell-free extracts by air-drying or treating with a solvent such as acetone and ether; or immobilized enzymes obtained by fixing the cells or the solid materials by per se known method in the field of biochemical reactors.

The conversion of apocarnitine into L-carnitine can also be conducted in an aqueous medium cultivating the said microorganisms.

Examples of the present invention are described in the following, however, the invention is not limited by these examples.

EXAMPLE 1

| Composition of culture medium | |
| --- | --- |
| Apocarnitine sulfate | 5.0 g |
| Glucose | 4.0 g |
| Peptone | 1.0 g |
| L-Asparagine | 2.0 g |
| $KH_2PO_4$ | 1.5 g |
| $CaCl_2.2H_2O$ | 0.3 g |
| $MgSO_4.7H_2O$ | 0.5 g |
| $(NH_4)_2SO_4$ | 2.0 g |
| Inorganic micronutrient solution[a] | 1.0 ml |
| Vitamin solution[b] | 10.0 ml |
| Deionized water | 989.0 ml |
| pH | 6.0 |

| [a]Inorganic micronutrient solution | |
| --- | --- |
| $H_3BO_3$ | 60 mg |
| $MnSO_4$ | 30 mg |
| $ZnSO_4.7H_2O$ | 300 mg |
| $CuSO_3$ | 40 mg |
| $FeCl_3.6H_2O$ | 250 mg |
| $Na_2MoO_4.2H_2O$ | 25 mg |
| Deionized water | 100 ml |
| [b]Vitamin solution | |
| Thiamine hydrochloride | 20 mg |
| Pyridoxine hydrochloride | 20 mg |
| Nicotinic acid | 20 mg |
| Pantoteinic acid | 20 mg |
| Biotin | 200 µg |
| Inositol | 1 g |
| Deionized water | 100 ml |

The above-mentioned culture medium is inoculated with the strain Y-239-b, and the shake culture is carried out at 30° C. for 48 hours. After the incubation, the resultant culture broth is centrifuged to give 1000 ml of the supernatant solution. The supernatant solution is adjusted to pH 8, and passed through a column of Diaion SK-IB, type H (produced by Mitsubishi Chemical Ind., Ltd., Tokyo), a strongly acid cation exchange resin, to allow the adsorption. Elution is carried out with 200 ml of 0.5N aqueous ammonia, and the eluate is concentrated under reduced pressure at 40° C. The concentrate is subject to high pressure liquid chromatography to separate the fraction containing L-carnitine, and the fraction is concentrated under reduced pressure to yield L-carnitine in the form of oil. The oily substance is recrystallized from methanol-acetone to give 500 mg of white crystals of L-canitine. L-carnitine thus obtained shows the following physical properties.

$[\alpha] = -30.5$ (c=1., aqueous solution).

Decomposition point, 197°–198° C.

Elemental analysis (%), for $C_7H_{15}NO_3$: Calcd.: C, 52.15; H, 9.38; N, 29.78. Found: C, 52.20; H, 9.35; N, 29.82.

EXAMPLE 2

The culture medium as used in Example 1 is inoculated with the strain Y-239-b, and culture is carried out at 30° C. for 48 hours. The microbial cells are obtained by centrifuging 600 ml of the resutant culture broth, washed three times with physiological saline and subjected to ultrasonic treatment at a temperature of not more than 10° C., followed by centrifugation. 50 ml of 0.1N potassium phosphate buffer is added to the resultant residue to give an enzyme solution. 50 μl of the enzyme solution is allowed to undergo reaction in a solution of 50 μl of 1% apocarnitine sulfate solution and 400 μl of 0.1N potassium phosphate buffer (pH 6.5) at 30° C. for 2.5 hours. Quantitative determination with use of TLC indicates that there is produced 180 μg of L-carnitine.

EXAMPLE 3

The culture medium as used in Example 1, which is free of apocarnitine sulfate, is inoculated with the strain Y-239-b, and after the incubation at 30° C. for 48 hours, the microbial cells are obtained by centrifuging the resultant cuture broth, washed with physiological saline, and subjected to the conventional treatment to prepare the acetone powder, whereby 440 mg of the acetone powder is obtained from 300 ml of the culture broth. 20 mg of acetone powder is allowed to undergo reaction in a solution of 20 μl of 10% apocarnitine sulfate solution and 980 μl of 0.1% potassium phosphate buffer (pH 6.5) at 30° C. for 3 hours, and quantitative determination is effected with use of TLC. As a result, it is revealed that there is produced 200 μg of L-carnitine per 20 mg of the acetone powder (from microbial cells).

We claim:

1. A process for preparing L-carnitine which comprises contacting apocarnitine with water in the presence of hydrase, said hydrase being produced by Enterobacter sp. Y-239-b or the mutant thereof and which is capable of hydrating apocarnitine, in an aqueous medium having a pH of 4–10 at a temperature of 20°–60° C.; and recovering L-carnitine from the aqueous medium.

2. A process according to claim 1 wherein the contacting is carried out in the aqueous culture of Enterobacter sp. Y-239-b or the mutant thereof at a temperature of 25°–30° C., the hydrase being contained in the culture.

3. A process according to claim 1 wherein the contacting is carried out in an aqueous medium containing the hydrase extracted from a culture of Enterobacter sp. Y-239-b or the mutant thereof.

4. A process according to claim 1 wherein the hydrase is employed in the form of cell-free extract from a culture of Enterobacter sp. Y-239-b or the mutant thereof.

5. A composition for producing L-carnitine comprising an aqueous medium containing apocarnitine and hydrase in an amount effective to convert apocarnitine to L-carnitine, the hydrase having been produced by Enterobacter sp. Y-239-b or the mutant thereof.

6. A composition according to claim 5 wherein the aqueous medium has a pH of 4–10 and a temperature of 20°–60° C.

7. A composition according to claim 5 wherein the aqueous medium is a culture medium of the strain.

* * * * *